United States Patent [19]

Schroeder

[11] Patent Number: 4,784,131
[45] Date of Patent: Nov. 15, 1988

[54] POLLEN PROTECTION DEVICE

[76] Inventor: Michael Schroeder, Konviktstrasse 10a, D-7800 Freiburg im Breisgau, Fed. Rep. of Germany

[21] Appl. No.: 931,131

[22] Filed: Nov. 17, 1986

[30] Foreign Application Priority Data

Mar. 17, 1986 [DE] Fed. Rep. of Germany ....... 3608872

[51] Int. Cl.$^4$ ............................................. A62B 23/02
[52] U.S. Cl. ........................... 128/206.16; 128/206.18; 2/426
[58] Field of Search .......... 128/205.15, 206.12.201.15, 128/206.15, 206.16, 206.18, 206.19, 201.17; 2/139, 426, 436, 437, 452, 422, 428, 431, 439

[56] References Cited

U.S. PATENT DOCUMENTS

| 152,218 | 6/1877 | Crofutt | 128/206.19 |
| 1,020,994 | 3/1912 | Leasure | 2/427 |
| 1,401,724 | 12/1921 | Dalij | 128/205.25 |
| 2,056,753 | 10/1936 | Wagner | 128/206.19 |
| 2,372,834 | 4/1945 | Kish | 128/201.15 |
| 2,792,000 | 5/1957 | Richardson | 128/201.15 |
| 2,877,463 | 3/1959 | Watkins | 2/437 |
| 3,298,031 | 1/1967 | Morgan | 2/427 |
| 4,004,884 | 1/1977 | Geaney | 128/206.18 |
| 4,098,270 | 7/1978 | Dolby | 128/206.12 |
| 4,176,410 | 12/1979 | Matthias | 2/439 |
| 4,447,914 | 5/1984 | Tannard | 2/436 |
| 4,674,136 | 6/1987 | Ladewig | 2/428 |

FOREIGN PATENT DOCUMENTS

| 2335160 | 1/1975 | Fed. Rep. of Germany | 128/206.12 |
| 935100 | 6/1982 | U.S.S.R. | 2/436 |
| 2035807 | 6/1980 | United Kingdom | 128/201.15 |

*Primary Examiner*—Edward M. Coven
*Assistant Examiner*—K. M. Reichle
*Attorney, Agent, or Firm*—Foley & Lardner, Schwartz, Jeffery, Schwaab, Mack, Blumenthal & Evans

[57] ABSTRACT

A pollen protection device comprising a holder and an elastic band for retaining the holder on the face of the user so as to enclose the eyes and nose. The holder is comprised of upper and lower flange walls in which are mounted filter members having a mesh size to pass air but not pollen, with additional filters being positioned between the walls at the sides thereof. Also mounted between the flange walls at the front is a viewing lens. A protective cloth impermeable to pollen can be secured to the lower flange wall and extends downwardly over the mouth and around the neck of the user to permit inhalation through the mouth.

7 Claims, 2 Drawing Sheets

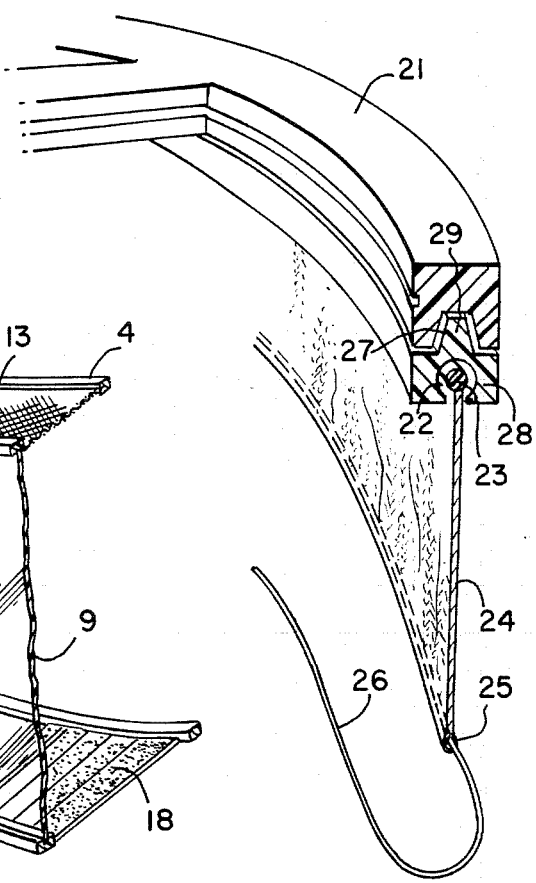
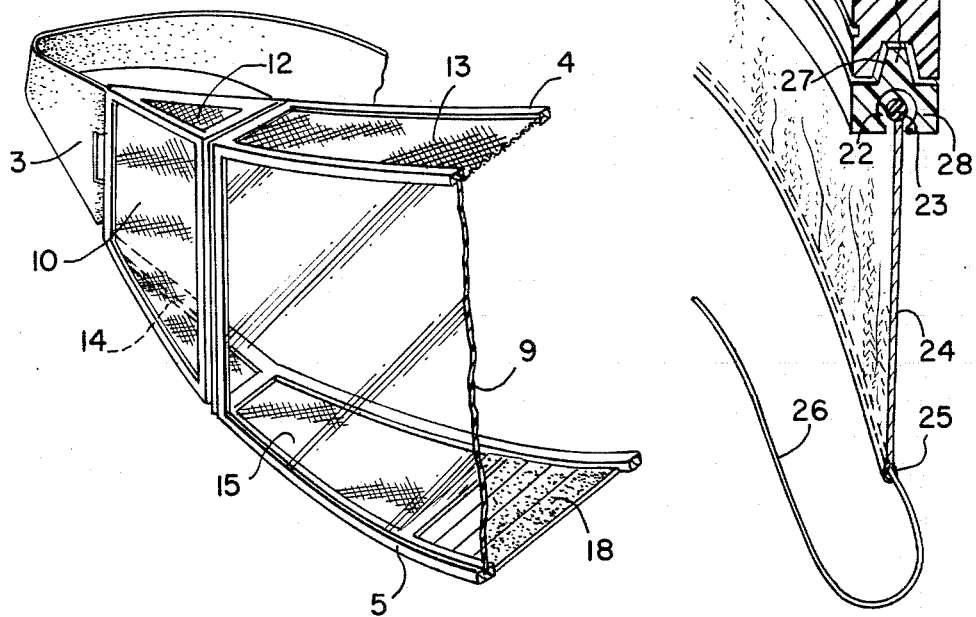
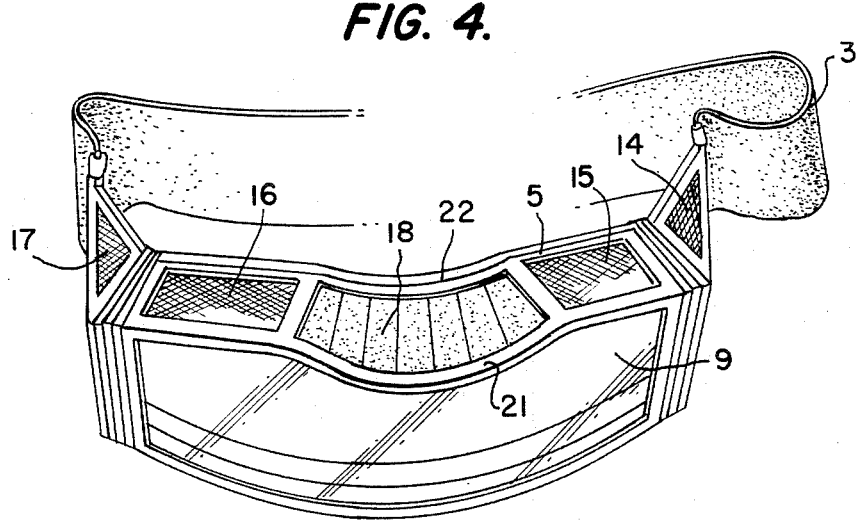

POLLEN PROTECTION DEVICE

BACKGROUND OF THE INVENTION

The invention relates to a pollen protection device intended to protect the mucous membranes of the eyes and the nose of allergic persons against contact with the pollen of flowers.

As the primary protection of persons sensitive to the pollen carried annually into the atmosphere during the flowering period of grasses, flowers, bushes and trees by the wind and thermal currents, heretofore two principal measures have become known in relation to their mechanical and allergic actions.

First, a pollen protection hood is known, consisting of a filter fabric comprising a sight window, in combination with a head covering. Such a hood cannot be worn in public without attracting attention and cannot be color coordinated esthetically with light summer clothing. Furthermore, the entire head of the wearer is masked which, particularly with high temperatures, leads to increased perspiration.

Secondly, conical plugs are known consisting of a foamed material to be introduced into the nasal openings. These plugs cause a disagreeable sensation as the result of their pressure against the nasal walls and cannot be considered harmless for hygienic reasons. In addition, they protect only the nasal mucosa and not the eyes which may also become strongly irritated by pollen.

SUMMARY OF THE INVENTION

The object of the present invention is to provide a device capable of effectively protecting both the eyes and the nose of persons allergic to pollen, which device is easily manipulated and usable without effects harmful to health. The device is capable of preventing the passage of pollen through the mouth into the throat, if breathing is taking place exclusively through the mouth because of a stopped up nose. The device also satisfies esthetic requirements.

The pollen protection device according to the invention has several advantages. It can be produced and marketed at the most in two sizes, one for children and one for adults; it may be integrated in the manner of sunglasses into any type of attire, i.e., professional, recreational or sports, without the need for additional measures; it is easily manipulated, and it can be stored in a small space when not in use. It is further possible to color coordinate the spectacles with clothing.

The air filter elements according to the invention are positioned in flange walls and/or the lateral web sections of the device and consist preferably of a galvanized metal foil with a mesh width of less than 40 $\mu$m. The filter elements thus form a plurality of passage orifices which retain by virtue of their size the pollen and allow the passage of breathing air. It has been found in actual practice that sufficient breathing air is available when using the device, if the entire air permeation surface amounts to at least 4 cm$^2$. There is no lack of oxygen even after a use of several hours.

Good aeration and ventilation of the space enclosed by the device is obtained in particular according to the invention if both the lower and the upper flange walls are equipped with air filters. In this case the air filter surfaces are essentially parallel to each other so that the passage orifices of the two filters are oriented in the same direction of flow. In addition, the placement of an air filter in the upper flange wall effects the rapid exhaust of the air exhaled, which due to its passage through the human body is generally warmer than the outside air and therefore rises within the space formed by the spectacle and the face upwards toward the upper flange wall and is able to escape immediately through the filter. The condensation of water droplets on the lens may be counteracted additionally by using a so-called antifogging glass for the lens.

A further feature of the protective device of the invention consists of a valve which allows the passage of exhaled air. The valve is preferably a rubber membrane and is set into the lower flange wall of the device. This valve, which is placed into its open position by the flow of air released by exhalation, makes possible the rapid exhaust of this air into the atmosphere. The open valve further permits the passage of very small droplets of water potentially formed in the space enclosed by the spectacle and entrained by the air exhaled.

The exhaled air is channeled advantageously according to the invention by two spaced apart air guide vanes extending from the inside of the lower flange wall, generally transversely to its longitudinal direction, said guide vanes flanking the nose of the user when the device is in use.

The invention is further characterized in that an undercut groove is formed in the outside of the lower flange wall, at the edge toward the open side of the holder. A connecting part in the form of a rail is adapted to fit in the groove, with the rail member being adapted to receive a rod which in turn carries a protective cloth. The cloth preferably extends downwardly to the neck of the user and is formed along its lower longitudinal edge with a hollow hem to receive a fastening cord by means of which the cloth can be tightened around the neck so as to surround the face. This protective cloth is used advantageously when breathing only through the mouth is possible, e.g., because of a stopped up nose. The protective cloth consists of a material permitting unimpaired breathing but which is impermeable to pollen.

A reliable, pollen tight seat of the protective spectacle held on the head of the user by means of a preferably elastic holding band is obtained by providing the free longitudinal edge of each flange wall with a cushion in the form of an elastic yielding sealing strip impermeable to pollen.

In an advantageous manner, the holder or frame of the protective device consists of a flexible material such as polyethylene, which cannot fracture easily and does not present a risk of injury to the user.

BRIEF DESCRIPTION OF THE DRAWINGS

The invention will become more apparent from the embodiments shown in the drawings, the figures of which are as follows:

FIG. 3 is a fragmented front perspective view of a modified protective spectacle;

FIG. 4 is a perspective view of the bottom of the spectacle of FIG. 2; and

FIG. 5 is an enlarged partial sectional view of the lower flange wall of the FIGS. 2 and 4 embodiment, with a protective cloth being attached thereto extending downwardly from the spectacle.

DETAILED DESCRIPTION OF THE PREFERRED EMBODIMENTS

Figure 1:
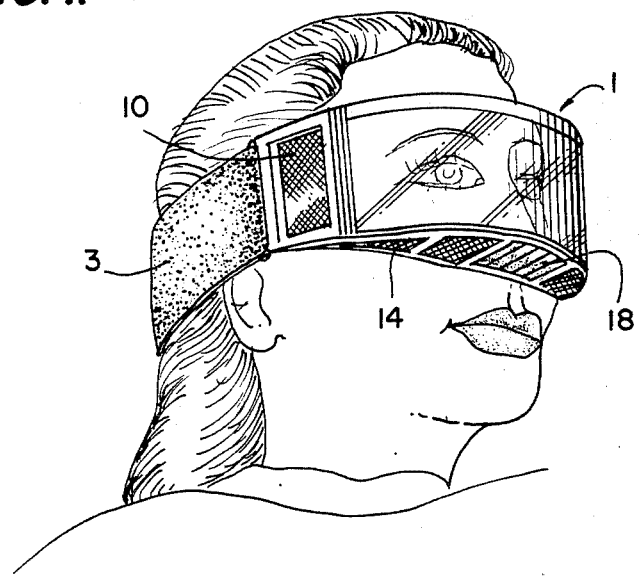
FIG. 1 shows a protective spectacle according to the invention, placed on the head of a user.
Figure 2:
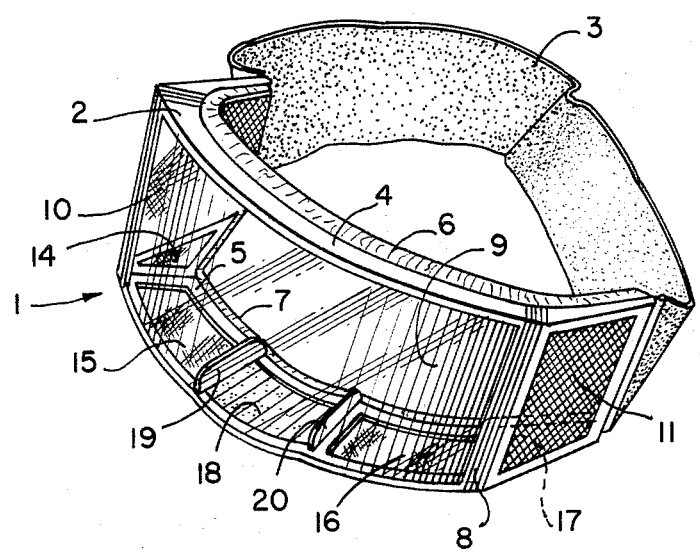
FIG. 2 is a perspective view of the spectacle.

The protective spectacle according to the embodiment of the invention shown in FIGS. 1, 2 and 4 is generally indicated at 1 and consists of a frame-like holder 2 made of a flexible material, such as polyethylene, and a holding band 3 secured to the holder and preferably consisting of a rubber or elastic material. The holder 2 has a generally crescent shaped horizontal projection. The two flange walls 4 and 5 of the holder 2 are curved in a concave manner along their inner longitudinal edges for better adaptation to the facial contours of the user, and in order to obtain a good, non-fatiguing seat the edges are each cushioned by an elastically yielding strip 6 and 7, respectively, which is impermeable to pollen. The strips can be secured to the flange walls by bonding or any other suitable manner.

The web 8 of the holder 2 consists for the most part of a sight lens 9 made of an unbreakable material, for example, polycarbonate. The two lateral web segments 10 and 11 are in the form of air filters.

Further air filter elements are preferably placed in openings 14, 15, 17 and 16 formed in the flange wall 5. The air filter elements consist preferably of galvanized metal foil with a mesh size of less than 40 $\mu$m.

In the center of the lower flange wall 5 a valve in the form of a rubber membrane 18 is provided (see FIG. 3). The membrane valve opens under the pressure of the air exhaled through the nose and closes during inhalation due to its flexible nature. Air guide vanes 19, 20 (FIG. 2) are arranged on either side of the rubber membrane transversely to the longitudinal direction of the lower flange wall 5, for flanking and accommodating the nose of the wearer. For purposes of clarity, the membrane 18 does not appear in FIG. 4.

Referring to FIG. 5, in the bottom surface 21 of the flange is formed a U-shaped groove 27 adapted to receive a rail member 28 having a projection 29 similar in shape to and engaged in the groove 27 by bonding or the like. The rail member is formed with an undercut groove 22 into which a rod 23 can be inserted. The rod 23 has secured thereto a permeable protective cloth 24 the height of which is such that it extends downwardly to the neck of the user. A seam 25 is formed in the bottom of the cloth which receives a fastening cord by means of which the cloth can be gathered about the lower face and neck of the user. The cloth 24 is impermeable to pollen.

Referring to FIG. 3, the embodiment shown there differs from the FIGS. 1, 2 and 4 form in that filter elements are also provided in the top flange wall 4. As shown, the top and bottom walls 4 and 5, respectively are similar in construction, with top wall 4 being provided with openings to receive filter elements 12 and 13 at one side of the flange wall, and similar openings and filters (not shown) at the opposite end of the flange wall. The openings and filters in the respective flange walls 4 and 5 are generally vertically aligned, filters 12, 13 and 14, 15, for example, so that vertical air flow through the filters are accommodated. In addition, the provision of filters in the upper flange wall 4 permits air exhaled by the user to be rapidly exhausted from the device.

What is claimed is:

1. A pollen protection device, comprising:
   (a) a frame-like holder which in use encloses the eyes and the nose of a user in a pollen-tight manner, said holder in a state of non-use being generally crescent shaped in horizontal cross section and formed of a flexible plastic material which can accommodate the shape of the face of the user, comprising:
   (1) a front web in which is mounted an eye protecting lens constructed of a material permitting viewing therethrough by the user, the vertical dimension of said lens being such that the eyes and nose of the user are accommodated within said lens,
   (2) upper and lower flange walls extending generally perpendicular to said front web and lens,
   (3) web sections at the sides of the holder forming continuations of said front web and extending between said flange walls,
   (4) air filter means mounted in each of said side web sections, said air filter means having a mesh less than 40 $\mu$m for filtering pollen and a filter area of at least sixteen square centimeters, and
   (b) elastic band means secured to said holder by means of which said upper and lower flange walls can be drawn snugly against the face of the wearer.

2. The device of claim 1 wherein at least one of said upper and lower flange walls is formed with a plurality of openings, and further air filter means are mounted in said openings to provide additional paths for filtered air.

3. The device of claim 2 wherein both of said upper and lower flange walls are formed with a plurality of openings, and further air filter means are inserted in the openings of both flange walls.

4. The pollen protection device of claim 1, wherein the inner surface of each of said flange walls adapted to contact the face of the user is concavely curved to generally conform to the curvature of the face of the user.

5. The pollen protection device of claim 4, wherein said concavely curved inner surface of each of the flange walls has mounted thereon an elastically yielding sealing strip impermeable to pollen for cushioning the holder against the face of the user.

6. The pollen protection device of claim 1, further including a groove formed in the edge on the open side of the lower flange wall of the holder, rod means mounted in said groove, and a protective cloth secured to said rod means and adapted to extend downwardly to the neck of the user, said cloth being formed on its lower longitudinal edge with a hollow hem, and a fastening cord positioned in said hollow hem to permit the protective cloth to be tightly gathered around the neck of the user.

7. The pollen protection device of claim 1, wherein said air filter means are comprised of galvanized metal foil.

* * * * *
* * * * *